US010864155B2

(12) United States Patent
Bai et al.

(10) Patent No.: US 10,864,155 B2
(45) Date of Patent: Dec. 15, 2020

(54) OIL CLEANSER COMPOSITION

(71) Applicants: Dow Global Technologies LLC, Midland, MI (US); Rohm and Haas Company, Collegeville, PA (US)

(72) Inventors: Lu Bai, Saginaw, MI (US); Liang Chen, Sewickley, PA (US); Yunshen Chen, Lexington, MA (US); Shannon Golden, Saginaw, MI (US); Jennifer Koenig, Lansdale, PA (US); Lyndsay M. Leal, Spring City, PA (US); Xiang Qian Liu, Collegeville, PA (US); Wen-Shiue Young, Lansdale, PA (US); Fanwen Zeng, Audubon, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/618,815

(22) PCT Filed: Jun. 13, 2018

(86) PCT No.: PCT/US2018/037290
§ 371 (c)(1),
(2) Date: Dec. 3, 2019

(87) PCT Pub. No.: WO2018/231953
PCT Pub. Date: Dec. 20, 2018

(65) Prior Publication Data
US 2020/0138689 A1 May 7, 2020

Related U.S. Application Data

(60) Provisional application No. 62/645,855, filed on Mar. 21, 2018, provisional application No. 62/549,098, filed on Aug. 23, 2017, provisional application No. 62/520,924, filed on Jun. 16, 2017.

(51) Int. Cl.
| | | |
|---|---|---|
| *A61K 8/81* | (2006.01) |
| *A61Q 19/10* | (2006.01) |
| *A61K 8/04* | (2006.01) |
| *A61K 8/37* | (2006.01) |
| *A61K 8/41* | (2006.01) |
| *A61K 8/46* | (2006.01) |

(52) U.S. Cl.
CPC ............ *A61K 8/8152* (2013.01); *A61K 8/042* (2013.01); *A61K 8/375* (2013.01); *A61K 8/41* (2013.01); *A61K 8/416* (2013.01); *A61K 8/463* (2013.01); *A61Q 19/10* (2013.01); *A61K 2800/48* (2013.01); *A61K 2800/596* (2013.01)

(58) Field of Classification Search
CPC ............................. A61K 8/8152; A61K 8/375
See application file for complete search history.

(56) References Cited

U.S. PATENT DOCUMENTS

| | | | |
|---|---|---|---|
| 4,542,171 A | 9/1985 | Elser et al. | |
| 5,710,161 A | 1/1998 | Ladduwahetty et al. | |
| 7,674,848 B2 | 3/2010 | Lin | |
| 9,439,848 B2* | 9/2016 | Graham | A61K 8/91 |
| 9,867,768 B2* | 1/2018 | Figura | A61K 8/89 |
| 2009/0196839 A1* | 8/2009 | Farcet | A61Q 1/06 424/59 |
| 2010/0178257 A1* | 7/2010 | Farcet | A61Q 1/02 424/59 |
| 2013/0259812 A1* | 10/2013 | Zeng | A61Q 3/02 424/59 |
| 2014/0113992 A1 | 4/2014 | Chen et al. | |
| 2014/0341960 A1 | 11/2014 | Hattori et al. | |
| 2014/0363385 A1* | 12/2014 | Zeng | C08F 220/68 424/60 |
| 2014/0364511 A1* | 12/2014 | Chari | C08K 5/20 514/772.6 |
| 2015/0342858 A1* | 12/2015 | Tamareselvy | A61K 8/8158 424/70.12 |
| 2016/0015622 A1* | 1/2016 | Rafferty | A61K 8/891 424/70.12 |
| 2016/0022566 A1* | 1/2016 | Figura | A61Q 5/12 510/122 |
| 2018/0161253 A1* | 6/2018 | Gilles | A61Q 5/06 |
| 2019/0274944 A1* | 9/2019 | Leal | A61K 8/46 |
| 2020/0138689 A1* | 5/2020 | Bai | A61K 8/8152 |
| 2020/0255568 A1* | 8/2020 | Hsu | C08F 220/1802 |

FOREIGN PATENT DOCUMENTS

| | | |
|---|---|---|
| EP | 0861657 B1 | 7/2000 |
| WO | 2013040167 A1 | 3/2013 |
| WO | 2014099512 A2 | 6/2014 |
| WO | 2014204937 A1 | 12/2014 |

* cited by examiner

*Primary Examiner* — Mark Eashoo
*Assistant Examiner* — M. Reza Asdjodi
(74) *Attorney, Agent, or Firm* — Edward L. Brant

(57) ABSTRACT

Provided are personal care compositions including (a) hydrophobic ester oil, (b) at least one of a nonionic or anionic surfactant, and (c) one or more polymers containing polymerized structural units of (i) 79 to 95.74 weight % of $C_4$-$C_8$ (meth)acrylate monomers, (ii) 0.5 to 5 weight % of (meth)acrylic acid monomer, (iii) 3.75 to 14 weight % of (methoxy) poly(ethylene glycol) methacrylates, and (iv) 0.01 to 2 weight % of at least one crosslinker.

7 Claims, No Drawings

OIL CLEANSER COMPOSITION

FIELD OF THE INVENTION

This invention relates generally to personal care compositions that are useful as oil cleansing formulations. The personal care compositions contain hydrophobic ester oil, a surfactant, and acrylic copolymers.

BACKGROUND

Personal care cleansing compositions contain a variety of additives that provide a wide array of benefits to the composition. One class of additives are oil thickeners that provide viscosity enhancements and impart good aesthetics, such as good sensory feel and clarity. Oil thickening agents that are known in the art include, for example, styrene-ethylene/butadiene-styrene copolymers, polyamide polymers, and cellulose-based polymers. These thickeners, however, come with certain drawbacks, including insufficient viscosity enhancement, high formulation temperature, and lack of consistency in viscosity control in consumer product formulations.

To this end, polyacrylate oil gels have been utilized in the art. For example, WO 2014/204937 A1 discloses personal care compositions comprising a polyacrylate oil gel containing a cosmetically acceptable hydrophobic ester oil and a polymer including at least two polymerized units. The prior art does not, however, disclose a polyacrylate oil gel according to the present invention which achieves the significant viscosity performance at low formulation temperatures while also providing a clear formulation.

Accordingly, there is a need to develop thickeners that provide significant viscosity enhancements, while not suffering from the drawbacks of the prior art.

STATEMENT OF INVENTION

One aspect of the invention provides a personal care composition comprising (a) at least one cosmetically acceptable hydrophobic ester oil, (b) at least one surfactant selected from the group consisting of nonionic surfactants, anionic surfactants, and mixtures thereof, and (c) one or more polymers comprising polymerized structural units of (i) 79 to 95.74 weight % of $C_4$-$C_8$ (meth)acrylate monomers, (ii) 0.5 to 5 weight % of (meth)acrylic acid monomer, (iii) 3.75 to 14 weight % of (methoxy) poly(ethylene glycol) methacrylates, and (iv) 0.01 to 2 weight % of at least one crosslinker.

In another aspect, the invention provides a personal care composition comprising (a) 50 to 70 weight % of one or more aliphatic $C_8$-$C_{24}$ alkyl triglycerides, (b) 30 to 50 weight % of a surfactant comprising a nonionic surfactant has a hydrophile-lipophile balance value of from 9 to 12, and a anionic alkyl ether sulfate surfactant selected from the group consisting of a triethanolamine salt, a monoisopropanolamine salt, and combinations thereof, and (c) 4 to 6 weight % of one or more polymers comprising polymerized units derived from (i) 84.5 to 91.45 weight % of i-butyl methacrylate and ethylhexyl methacrylate, (ii) 1 to 3 weight % of (meth)acrylic acid monomer, (iii) 7.5 to 12.5 weight % of (methoxy) poly(ethylene glycol) methacrylate having a weight average molecular weight of from 300 to 600, and (iv) 0.05 to 0.3 weight % of trimethylol propane trimethacrylate.

DETAILED DESCRIPTION

The inventors have now surprisingly found that personal care compositions comprising hydrophobic ester oil, surfactant, and polymers having a high weight percent of polymerized units derived from $C_4$-$C_8$ (meth)acrylate monomer, (methoxy) poly(ethylene glycol) methacrylates, and a small weight percent of (meth)acrylic acid monomer, provide significant viscosity enhancements while retaining clarity in personal care cleansing formulations. Accordingly, the present invention provides in one aspect a personal care cleansing composition comprising (a) hydrophobic oil ester, and (b) at least one a nonionic or anionic alkyl ether sulfate surfactant, and (c) one or more polymers comprising polymerized units derived from (i) 79 to 95.74 weight % of $C_4$-$C_8$ (meth)acrylate monomers, (ii) 0.5 to 5 weight % of (meth)acrylic acid monomer, (iii) 3.75 to 14 weight % of (methoxy) poly(ethylene glycol) methacrylates, and (iv) 0.01 to 2 weight % of at least one crosslinker.

In the present invention, "personal care" is intended to refer to cosmetic and skin care compositions for application to the skin, including, for example, body washes and cleansers, as well as leave on application to the skin, such as lotions, creams, gels, gel creams, serums, toners, wipes, liquid foundations, make-ups, tinted moisturizer, oils, face/body sprays, and topical medicines. In the present invention, "personal care" is also intended to refer to hair care compositions including, for example, shampoos, leave-on conditioners, rinse-off conditioners, styling gels, pomades, hair coloring products (e.g., two-part hair dyes), hairsprays, and mousses. Preferably, the personal care composition is cosmetically acceptable. "Cosmetically acceptable" refers to ingredients typically used in personal care compositions, and is intended to underscore that materials that are toxic when present in the amounts typically found in personal care compositions are not contemplated as part of the present disclosure. The compositions of the invention may be manufactured by processes well known in the art, for example, by means of conventional mixing, dissolving, granulating, emulsifying, encapsulating, entrapping or lyophilizing processes.

As used herein, the term "polymer" refers to a polymeric compound prepared by polymerizing monomers, whether of the same or a different type. The generic term "polymer" includes the terms "homopolymer," "copolymer," and "terpolymer." As used herein, the term "polymerized structural units" of a given monomer refers to the remnant of the monomer after polymerization. As used herein, the term "(meth)acrylate" refers to either acrylate or methacrylate, and the term "(meth)acrylic" refers to either acrylic or methacrylic. Similarly, as used herein, the term "(methoxy) poly(ethylene glycol) (meth)acrylate" refers to either methoxy poly(ethylene glycol)(meth)acrylate or poly(ethylene glycol)(meth)acrylate. As used herein, the term "substituted" refers to having at least one attached chemical group, for example, alkyl group, alkenyl group, vinyl group, hydroxyl group, carboxylic acid group, other functional groups, and combinations thereof.

As used herein, the term "hydrophile-lipophile balance (HLB) value" refers to the value calculated from the mol fraction in a nonionic surfactant mixture starting from its concentration in a mixture in weight % followed by calculation of the concentration in mol by dividing the concentration by molecular weight of the surfactants. The total nonionic surfactant concentration in mol is calculated and mol fraction of each surfactant in the mixture is calculated by dividing the mol concentration of a surfactant in the mixture by the total nonionic surfactant concentration in mol. In order to calculate the system HLB value, subsequently, the mol fraction of each non-ionic surfactant is multiplied by its HLB value and the sum of the resulting numbers is the system HLB value.

The inventive personal care compositions include one or more polymers comprising structural units of $C_4$-$C_8$ (meth)acrylate monomers, (meth)acrylic acid monomers, and (methoxy) poly(ethylene glycol) methacrylates. Suitable $C_4$-$C_8$ (meth)acrylate monomers include, for example, n-butyl (meth)acrylate, i-butyl (meth)acrylate, 2-ethylhexyl (meth)acrylate, cyclohexyl (meth)acrylate, n-octyl (meth)acrylate, phenyl (meth)acrylate, benzyl (meth)acrylate, and 2-phenylethyl (meth)acrylate. Preferably, the $C_4$-$C_8$ (meth)acrylate monomers comprise one or more of i-butyl methacrylate, n-butyl methacrylate, and ethylhexyl methacrylate. In certain embodiments, the polymer comprises polymerized structural units of $C_4$-$C_8$ (meth)acrylate monomers in an amount of from 79 to 95.74 weight %, preferably from 73.5 to 94 weight %, and more preferably from 84.5 to 91.45 weight %, based on the total weight of the polymer. In certain embodiments, the $C_4$-$C_8$ (meth)acrylate monomers comprise i-butyl methacrylate and ethylhexyl methacrylate in a ratio of from 9:1 to 2:3, preferably from 3:2 to 2:3, and more preferably 1:1.

The polymers of the inventive personal care compositions also comprise structural units of (meth)acrylic acid monomer. In certain embodiments, the polymer comprises polymerized structural units of (meth)acrylic acid monomer in an amount of from 0.5 to 5 weight %, preferably from 0.8 to 4 weight %, and more preferably from 1 to 3 weight %, based on the total weight of the polymer.

The polymers of the inventive personal care composition also comprise structural units of (methoxy) poly(ethylene glycol) methacrylates. In certain embodiments, the (methoxy) poly(ethylene glycol) methacrylates comprise one or more of methoxy-poly(ethylene glycol) (meth)acrylate and poly(ethylene glycol) (meth)acrylate ("PEGMA"). In certain embodiments, the (methoxy) poly(ethylene glycol) (meth)acrylate comprises methoxy-poly(ethylene glycol) monomethacrylate. Commercially available (methoxy) poly(ethylene glycol) (meth)acrylates include, for example: methoxy poly(ethylene glycol) monomethacrylates of molecular weights of 300, 475, 1100, or 2100 or methoxy poly(ethylene glycol) monoacrylate having an molecular weight of 426 from Aldrich Chemical Co. of Milwaukee, Wis., U.S.A.; Visiomer® MPEG 750 MA, MPEG 1005 MA and MPEG 2005 from Evonik CYRO LLC of Osceola, Ark., U.S.A.; SR 550, CD 551, CD 552 or CD 553 from Sartomer Chemicals of Exton, Pa., U.S.A.; M-90G, M-230G, AM-90G (methoxy poly(ethylene glycol 400) monoacrylate or AM-230G from Shin-Nakamura Chemicals of Wakayama, Japan; Bisomer® PEM6 LD, PPMS LI, MPEG350MA, MPEG550MA, S7W, S10W or S20W from Cognis Corporation of Cincinnati, Ohio; and poly(ethylene glycol) monomethacrylates having molecular weights of 200 or 400 and methoxy poly(ethylene glycol) monomethacrylate having molecular weights of 200, 400 or 1000, from Polysciences, Inc. of Warrington, Pa., U.S.A. The poly(ethylene glycol) methacrylate suitable for use in the present invention has a weight average molecular weight ($M_w$) of from 100 to 4000 g/mol, preferably of from 200 to 2300 g/mol, and more preferably of from 300 to 600 g/mol as measured by gel permeation chromatography. In certain embodiments, the polymer comprises polymerized structural units of the (methoxy) poly(ethylene glycol) methacrylates in an amount of from 3.75 to 14 weight %, preferably from 5.5 to 13.25 weight %, and more preferably from 7.5 to 12.5 weight %, based on the total weight of the polymer.

The polymers of the inventive personal care composition also comprise polymerized structural units of at least one crosslinker. Crosslinkers are monomers having two or more non-conjugated ethylenically unsaturated groups. Suitable crosslinkers include, for example, di- or tri-allyl ethers and di- or tri-(meth)acrylyl esters of diols or polyols (e.g., trimethylolpropane diallyl ether (TMPDE), trimethylol propane trimethacrylate (TMPTMA), ethylene glycol dimethacrylate (EGDMA), diethylene glycol dimethacylate (DE-GDMA), 1,6-hexanediol dimethacrylate, polyethylene glycol diacrylate, and polypropylene glycol dimethacrylate), di- or tri-allyl esters of di- or tri-acids (e.g., diallyl phthalate), allyl (meth)acrylate, divinyl sulfone, triallyl phosphate, and divinylaromatics (e.g., divinylbenzene). In certain embodiments, the crosslinker comprises trimethylolpropane trimethacrylate. In certain embodiments, the crosslinker comprises polypropylene glycol dimethacrylate. In certain embodiments, the inventive copolymers comprise structural units of crosslinker monomers in an amount of from 0.01 to 2 weight %, preferably from 0.03 to 1.15 weight %, and more preferably 0.05 to 0.3 weight %, based on the total weight of the polymer.

In certain embodiments, the polymers have an average particle size of from 50 to 2000 nm, preferably of from 75 to 1125 nm, and more preferably of from 100 to 250 nm. Polymer molecular weights can be measured by standard methods such as, for example, size exclusion chromatography or intrinsic viscosity. In certain embodiments, the polymers are present in the personal care composition in an amount of from 0.1 to 20 weight %, preferably from 2 to 13, and more preferably from 4 to 6 weight %, based on the total weight of the personal care composition.

Suitable polymerization techniques for preparing the polymers contained in the inventive personal care compositions include, for example, emulsion polymerization and solution polymerization, preferably emulsion polymerization, as disclosed in U.S. Pat. No. 6,710,161. Aqueous emulsion polymerization processes typically are conducted in an aqueous reaction mixture, which contains at least one monomer and various synthesis adjuvants, such as the free radical sources, buffers, and reductants in an aqueous reaction medium. In certain embodiments, a chain transfer agent may be used to limit molecular weight. The aqueous reaction medium is the continuous fluid phase of the aqueous reaction mixture and contains more than 50 weight % water and optionally one or more water miscible solvents, based on the weight of the aqueous reaction medium. Suitable water miscible solvents include, for example, methanol, ethanol, propanol, acetone, ethylene glycol ethyl ethers, propylene glycol propyl ethers, and diacetone alcohol. In certain embodiments, the aqueous reaction medium contains more than 90 weight % water, preferably more than 95 weight % water, and more preferably more than 98 weight % water, based on the weight of the aqueous reaction medium.

The polymers of the present invention may be isolated by a spray drying process. While spray drying is one preferred embodiment of how to produce the dry powder, other suitable methods include, for example, freeze drying, a two-step process including the steps of (i) pan drying the emulsion and then (ii) grinding the pan dried material into a fine powder, coagulation of the acrylic emulsion and collection of the powder by filtration followed by washing and drying, fluid bed drying, roll drying, and freeze drying. Suitable techniques for spray drying the polymer beads of the present invention are known in the art, for example, as described in U.S. 2014/0113992 A1. In certain embodiments, anti-caking agents are used when spray drying the polymer beads. Suitable anti-caking agents include, for example, mineral fillers (e.g., calcium carbonate, kaolin, titanium oxide, talc, hydrated alumina, bentonite, and silica), solid polymer particles with a $T_g$ or $T_m$ greater than 60° C. (e.g., polymethylmethacrylate, polystyrene, and high density polyethylene), and water soluble polymers with a $T_g$ greater than 60° C. (e.g., polyvinyl alcohol and methylcellulose). The anti-caking agent can be mixed in the acrylic suspension prior to spray drying or introduced as a dry powder in the spray drying process. In certain embodiments, the anti-caking agent coats the polymer beads to prevent the beads from sticking to each other inner wall of the dryer. In certain embodiments, the anti-caking agent is present in an amount of from 0 to 20 weight %, and more preferably from 0.01 to 10 weight %, based on the total weight of the polymer beads.

The personal care compositions of the present invention also contain a cosmetically acceptable hydrophobic ester oil. In general, any hydrophobic ester oil or mixtures thereof which are toxicologically safe for human or animal use may constitute the oil base of the present invention. In certain embodiments, the hydrophobic ester oil comprises aliphatic $C_8$-$C_{24}$ alkyl triglycerides. Suitable hydrophobic ester oils include, for example, caprylic/capric triglycerides, saturated fatty esters and diesters (e.g., isopropyl palmitate, octyl palmitate, butyl stearate, isocetyl stearate, octadodecyl stearate, octadodecyl stearoyl stearate, diisopropyl adipate, and dioctyl sebacate), and animal oils and vegetable oils (e.g., mink oil, coconut oil, soybean oil, palm oil, corn oil, cocoa butter, sesame oil, sunflower seed oil, jojoba oil, olive oil, and lanolin oil). In certain embodiments, the hydrophobic ester oil is diffused in an oil base. Suitable oil bases include any oil or mixture of oils which are conventionally used in personal care products including, for example, paraffin oils, paraffin waxes, and fatty alcohols (e.g., stearyl alcohol, isostearyl alcohol, and isocetyl alcohol). In certain preferred embodiments, the hydrophobic ester oil comprises one or more of caprylic/capric triglycerides and sunflower seed oil. In certain embodiments, the hydrophobic ester oils are present in the personal care composition in an amount of from 10 to 90 weight %, preferably from 30 to 80 weight %, and more preferably from 50 to 70 weight %, based on the total weight of the personal care composition.

The personal care compositions of the present invention also contain at least one of nonionic surfactants, anionic surfactants, and mixtures thereof. In certain embodiments, the total amount of surfactant is present in an amount of 10 to 90 weight %, preferably from 20 to 70 weight %, and more preferably from 30 to 50 weight %, based on the total weight of the personal care composition. In certain embodiments, the nonionic surfactant and anionic surfactant are present in a ratio of from 1:15 to 10:1, preferably from 1:2 to 5:1, more preferably from 1:3 to 2:1, and more preferably from 1:4 to 1:1.

In certain embodiments, the nonionic surfactant has an HLB value of from 7 to 14, preferably from 8 to 13, and more preferably from 9 to 12, calculated from the mol fraction of individual nonionic surfactants in the nonionic surfactant mixture and the individual HLB values of nonionic surfactant. Suitable nonionic surfactants having such HLB values include, for example, those provided in Table 1.

TABLE 1

HLB Values of Non-ionic Surfactants

| Surfactant | HLB Value |
| --- | --- |
| PEG-8 Dioleate | 8 |
| Sorbitan Laurate | 8.6 |
| PEG-40 Sorbitan Peroleate | 9 |
| Laureth-4 | 9.7 |
| PEG-7 Glyceryl Cocoate | 10 |
| PEG-20 Almond Glycerides | 10 |
| PEG-25 Hydrogenated Castor Oil | 10.8 |
| Stearamide MEA | 11 |
| Polysorbate 85 | 11 |
| PEG-7 Olivate | 11 |
| Cetearyl Glucoside | 11 |
| Sorbeth-30 Tetraoleate | 11.5 |
| PEG-8 Oleate | 11.6 |
| Oleth-10 | 12.4 |
| Ceteth-10 | 12.9 |
| PEG-8 Laurate | 13 |
| Cocamide MEA | 13.5 |

In certain embodiments, suitable nonionic surfactants include, for example, sorbitan esters, (e.g., polyethylene glycol sorbitan stearic acid ester), fatty acid polyglycol esters or poly-condensates of ethyleneoxide and propyleneoixde.

Other suitable nonionic surfactants include, for example, long-chain fatty acid mono- and dialkanolamides, e.g., behenoyl monoethanolamide, coco monoethanolamide, isostearoyl monoethanolamide, lauroyl monoethanolamide, myristoyl monoethanolamide, oleoyl monoethanolamide, ricinoleoyl monoethanolamide, stearoyl monoethanolamide, behenoyl diethanolamide, caproyl diethanolamide, cocoyl diethanolamide, isostearoyl diethanolamide, lauroyl diethanolamide, lineloyl monoethanolamide, myristoyl monoethanolamide, oleoyl monoethanolamide, palmitoyl diethanolamide, ricinoleoyl monoethanolamide, and stearoyl monoethanolamide. Other suitable nonionic surfactants include, for example, $C_{10}$-$C_{22}$ fatty alcohol ethoxylates, e.g., oleth-2, oleth-3, oleth-4, oleth-5, oleth-6, oleth-7, oleth-8, oleth-9, oleth-10, oleth-11, oleth-12, oleth-15, oleth-16, oleth-20, oleth-25, laureth-2, laureth-3, laureth-4, laureth-5, laureth-6, laureth-7, laureth-8, laureth-9, laureth-10, laureth-11, laureth-12, laureth-13, laureth-15, laureth-16, laureth-20, laureth-25, ceteth-10, ceteth-12, ceteth-14, ceteth-15, ceteth-16, ceteth-17, ceteth-20, ceteth-25, cetoleth-10, cetoleth-12, cetoleth-14, cetoleth-15, cetoleth-16, cetoleth-17, cetoleth-20, cetoleth-25, ceteareth-10, ceteareth-12, ceteareth-14, ceteareth-15, ceteareth-16, ceteareth-18, ceteareth-20, ceteareth-22, ceteareth-25, isosteareth-10, isosteareth-12, isosteareth-15, isosteareth-20, isosteareth-22, isosteareth-25, steareth-10, steareth-11, steareth-14, steareth-15, steareth-16, steareth-20, and steareth-25. Other suitable nonionic surfactants include, for example, alkyl polyglucosides, e.g., decyl glucoside, carpylyl glucoside, ceteary glucoside, cocoyl ethyl glucoside, lauryl glucoside, myristyl glucoside, and coco glucoside. Other suitable nonionic surfactants include, for example, polyalkylene glycol ethers of fatty acid glyceride or partial glyceride, e.g., PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, and PEG-100 castor oil.

Anionic surfactants as used herein include substances having a negatively charged hydrophobe or that carry a negative charge when the pH is elevated to neutrality or above. Suitable anionic surfactants of the present invention include, for example, anionic alkyl ether sulfate surfactants (e.g., triethanolamine ("TEA") salts and monoisopropanolamine ("MIPA") salts), alkyl ether sulfonate surfactants, and alkyl ether carboxylate surfactants. Suitable anionic alkyl ether sulfate surfactants include, for example, ammonium capryleth sulfate, ammonium $C_{12}$-$C_{15}$ pareth sulfate, ammonium laureth sulfate, ammonium laureth-5 sulfate, ammonium myreth sulfate, DEA $C_{12}$-$C_{13}$ pareth-3 sulfate, DEA laureth sulfate, DEA myreth sulfate, diethylamine laureth sulfate, magnesium coceth sulfate, magnesium laureth sulfate, magnesium laureth-5 sulfate, magnesium myreth sulfate, magnesium oleth sulfate, MEA laureth sulfate, MIPA $C_{12}$-$C_{15}$ pareth sulfate, MIPA laureth sulfate, sodium coceth sulfate, sodium C9-15 pareth-3 sulfate, sodium $C_{10}$-$C_{15}$ is pareth-3 sulfate, sodium $C_{12}C_{16}$ pareth-2 sulfate, sodium $C_{12}$-$C_{13}$ pareth sulfate, sodium $C_{12}$-$C_{14}$ pareth-3 sulfate, sodium $C_{12}$-$C_{15}$ pareth sulfate, sodium $C_{12}$-$C_{15}$ pareth-3 sulfate, sodium $C_{13}$-$C_{15}$ pareth-3 sulfate, sodium doceth sulfate, sodium laneth sulfate, sodium laureth sulfate, sodium laureth-5 sulfate, sodium myreth sulfate, sodium oleth sulfate, TEA laureth sulfate, TEA laneth sulfate, and TIPA laureth sulfate.

Suitable anionic surfactants of the present invention also include, for example, acyl glutamates, acyl peptides, sarcosinates, taurates, carboxylic acids and salts thereof (e.g., alkanolic acids and alkanoates, ester carboxylic acids, and ether carboxylic acids), phosphoric acid ester and salts thereof, sulfonic acids and salts thereof (e.g., acyl isethionates, alkylaryl sulfonates, alkyl sulfonates, and sulfosuccinates), mono-basic salts of acyl glutamates that are slightly acidic in aqueous solution (e.g., sodium acyl glutamate and sodium hydrogenated tallow glutamate), salts of acyl-hydrolyzed protein (e.g., potassium, palmitoyl hydrolyzed milk protein, sodium cocoyl hydrolyzed soy protein, and TEA-abietoyl hydrolyzed collagen), salts of acyl sarcosinates (e.g., ammonium myristoyl sarcosine, sodium cocoyl sarcosinate, and TEA-lauroyl sarcosinate), salts of sodium methyl acyltaurates (e.g., sodium lauroyl taurate and sodium methyl cocoyl taurate), alkanoic acids and alkanoates (e.g., fatty acids derived from animal and vegetable glycerides that form water-soluble soaps and water-insoluble emulsifying soaps, including sodium stearate, aluminum stearate, and zinc undecylenate), ester carboxylic acids, (e.g., dinonoxynol-9-citrate), salts of acyl lactylates (e.g., calcium stearoyl lactylate and laureth-6 citrate), ethercarboxylic acids derived from ethyoxylated alcohols or phenols having varying lengths of polyoxyethylene chains (e.g., nonoxynol-8 carboxylic acid and sodium trideceth-13 carboxylate), mono- and di-esters of phosphoric acid and their salts (e.g., phospholipids, dilaureth-4-phosphate, DEA-oleth-10 phosphate, and triethanolamine lauryl phosphate), salts of acylisethionate (e.g., sodium cocoyl isethionate), alkylarylbenzene sulfonates (e.g., alpha-olefin sulfonate (AOS) and alkali metal, alkaline earth metal, and alkanolamine salts thereof, and sodium dodecylbenzene sulfonate), alkyl sulfonates (e.g., sodium $C_{12}$-$C_{14}$ olefin sulfonate, sodium cocomonoglyceride sulfonate, sodium $C_{12}$-$C_{15}$ pareth-15 sulfonate, and sodium lauryl sulfoacetate), sulfosuccinates (e.g., mono- and di-esters of sulfosuccinic acid, salts thereof and alkoxylated alkyl and alkylamido derivatives thereof, such as di-C4-Cio alkyl sodium sulfosuccinate, disodium laureth sulfosuccinate, disodium oleamido MEA-sulfosuccinate, and disodium $C_{12}$-$_{15}$ pareth sulfosuccinate, and the like).

The personal care compositions according to the present invention may be formulated by conventional mixing processes known to those skilled in the art. In certain embodiments, the formulation temperature is from 20° C. to 100° C., preferably from 25° C. to 50° C.

The inventive personal care compositions also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, glycols, such as propylene glycol, glycerin or the like, creams, aqueous solutions, oils, ointments, pastes, gels, lotions, milks, foams, suspensions, powders, or mixtures thereof. The aqueous solutions may contain cosolvents, e.g., water miscible cosolvents. Suitable water miscible cosolvents include, for example, ethanol, propanol, acetone, ethylene glycol ethyl ethers, propylene glycol propyl ethers, and diacetone alcohol. In some embodiments, the composition contains from about 99.99 to about 50 percent by weight of the dermatologically acceptable carrier, based on the total weight of the composition.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, eucalyptus oil, eugenol, menthyl lactate, witch hazel distillate), preservatives, anti-caking agents, a foam building agent, antifoaming agents, antimicrobial agents (e.g., iodopropyl butylcarbamate), anti-oxidants, binders, biological additives, buffering agents, bulking agents, chelating agents, chemical additives, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, vitamins (e.g., Vitamin C) and derivatives thereof, silicones, and fatty alcohols. The amount of option ingredients effective for achieving the desired property provided by such ingredients can be readily determined by one skilled in the art.

Some embodiments of the invention will now be described in detail in the following Examples.

EXAMPLES

Example 1

Preparation of Exemplary Polymer and Comparative Polymers

Exemplary polymers in accordance with the present invention and comparative polymers contain the components recited in Table 2.

TABLE 2

Exemplary and Comparative Polymers Particles

| Sample | Monomer (pbw) |
|---|---|
| P1 | 45.25 iBMA/45.25 EHMA/2 MAA/7.5 Methoxy-PEGMA (500)// 0.125 TMPTMA |
| P2 | 45.25 iBMA/45.25 EHMA/2 MAA/7.5 Methoxy-PEGMA (360)// 0.125 TMPTMA |
| P3 | 45.25 iBMA/45.25 EHMA/2 MAA/7.5 Methoxy-PEGMA (360)// 0.25 TMPTMA |
| P4 | 44 iBMA/44 EHMA/2 MAA/10 Methoxy-PEGMA (360)// 0.125 TMPTMA |
| P5 | 44 iBMA/44 EHMA/2 MAA/10 Methoxy-PEGMA (500)// 0.125 TMPTMA |
| P6 | 45.25 iBMA/45.25 EHMA/2 MAA/7.5 Methoxy-PEGMA (500)// 0.2 PPGDMA |
| C1*+ | 49 iBMA/49 EHMA/2 MAA//0.125 TMPTMA |
| C2*+ | 41.5 iBMA/41.5 EHMA/2 MAA/15 Methoxy-PEGMA (500)// 0.25 TMPTMA |
| C3*+ | 41.5 iBMA/41.5 EHMA/2 MAA/15 Methoxy-PEGMA (360)// 0.125 TMPTMA |
| C4*+ | 41.5 iBMA/41.5 EHMA/2 MAA/15 Methoxy-PEGMA (360)// 0.25 TMPTMA | iBMA = isobutyl methacrylate
EHMA = ethylhexyl methacrylate
MAA = methacrylic acid
Methoxy-PEGMA (500) = methoxy-poly(ethylene glycol) methacrylate, $M_w$ = 500
Methoxy-PEGMA (360) = methoxy-poly(ethylene glycol) methacrylate, $M_w$ = 360
TMPTMA = trimethylol propane trimethacrylate
PPGDMA = polypropylene glycol dimethacrylate, $M_w$ = 400
*Comparative
+Precipitated in formulation Synthesis of exemplary polymer P5 was carried out as follows. A three liter round bottom flask was equipped with a mechanical overhead stirrer, heating mantle, thermocouple, condenser and inlets for the addition of monomer, initiator and nitrogen. The kettle was charged with 900 grams deionized water and 7.46 grams of DS-4 (Polystep A-16-22: sodium dodecylbenzene sulfonate from Stepan). The kettle contents were set to stir with a nitrogen flow and heated to 87-89° C. To a plastic lined vessel, 17.68 grams of DS-4 and 256.65 grams deionized water was added and mixed with overhead stirring. 248.86 grams of Isobutyl Methacrylate, 248.86 grams of 2-Ethylhexyl Methacrylate, 56.65 grams of Poly (ethylene glycol) methacrylate (Mn 500, from Sigma-Aldrich), 11.31 grams of Methacrylic Acid, and 0.71 grams of Trimethylolpropane Trimethacrylate, were charged to the vessel and allowed to form a smooth, stable monomer emulsion. An initial catalyst charge of 0.28 grams of ammonium persulfate and 12.71 grams of deionized water was prepared and set aside. A kettle buffer solution of 1.92 grams of ammonium bicarbonate and 12.71 grams of deionized water was prepared and set aside. A preform seed of 22.38 grams was removed from the stable monomer emulsion and put into a small beaker. A line rinse of 16.8 grams of deionized water was prepared. A co-feed catalyst charge of 0.28 grams of ammonium persulfate and 49.22 grams of deionized water was prepared and set aside.

When the kettle was at temperature, the kettle buffer solution and initial catalyst solution were added to the reactor, followed by the preform seed and a rinse of 16.80 grams of deionized water. The reaction was monitored for a small exotherm. After the exotherm, the temperature control was adjusted to 83-85° C. The monomer emulsion feed was added to the kettle, sub-surface, at a rate of 4.95 grams/minute for 15 minutes. After 15 minutes, the rate was increased to 9.90 grams/minute for 75 minutes, giving a total feed time of 90 minutes. While the monomer emulsion feed was added to the kettle, the co-feed catalyst solution was also added over 90 minutes at a rate of 0.55 grams/minute. At the completion of the feeds, the previously prepared line rinse was added. The reaction was then held for 20 minutes at 83-85° C.

During the hold, a chase promoter of 3.77 grams of a 0.15% iron sulfate heptahydrate solution was prepared. A chase activator solution of 1.12 grams of isoascorbic acid dissolved in 36.40 grams of deionized water was prepared. A chase catalyst solution of 2.14 grams of 70% tert-butyl hydroperoxide in 35.40 grams of deionized water was prepared.

After the 20 minute hold, the reaction was cooled to 80° C. and a chase promoter solution was added as a shot to the kettle. The kettle contents were then slowly cooled to 70° C., while adding the chase activator and chase catalyst solutions separately by syringe over 60 minutes at a feed rate of 0.70 grams/minute. The reaction was held for 10 minutes, and then cooled to room temperature. At room temperature, the emulsion was filtered through a 100 mesh bag.

Exemplary polymers P1, P2, P3, P4, and comparative polymers C1, C2, C3 and C4 were prepared substantially as described above, with the appropriate changes in monomer and monomer amounts as recited in Table 2.

Example 2

Particle Size Characterization of Exemplary Polymers

Exemplary and comparative polymers as prepared in Example 1 were evaluated for particle size as shown in Table 3.

TABLE 3

Particle Size Characterization

| Sample | Particle Size (nm) |
|---|---|
| P1 | 118 |
| P2 | 111 |
| P3 | 106 |
| P4 | 106 |
| P5 | 115 |
| P6 | 114 |
| C1 | 131 |
| C2 | 103 |
| C3 | 130 |
| C4 | 102 |

The particle size distributions was determined by light scattering using a Malvern Mastersizer 2000 Analyzer equipped with a 2000uP module. Approximately 0.5 g of polymer emulsion samples were pre-diluted into 5 mL of 0.2 weight % active Triton 405 in degassed, DI water (diluents). The pre-diluted sample was added drop-wise to the diluent filled 2000uP module while the module was pumped at 1100 rpm. Red light obscurations were targeted to be between 4 and 8%. Samples were analyzed using a Mie scattering module (particle real refractive index of 1.48 and absorption of zerp: Diluent real refractive index of 1.330 with absorption of zero). A general purpose (spherical) analysis model with "normal sensitivity" was used to analyze the diffraction patterns and convert them into particle size distributions.

Example 3

Spray Drying of Exemplary and Comparative Polymers

Exemplary and comparative polymers as prepared in Example 1 were spray dried according to the following procedure. A two-fluid nozzle atomizer was equipped on a Mobile Minor spray dryer (GEA Process Engineering Inc.). The spray drying experiments were performed under an inert atmosphere of nitrogen. The nitrogen supplied to the atomizer at ambient temperature was set at 1 bar and 50% flow, which is equivalent to 6.0 kg/hour of flow rate. The polymer emulsion was fed into the atomizer at about 30 mL/min using a peristaltic pump (Masterflex L/S). Heated nitrogen was used to evaporate the water. The inlet temperature was set at 140° C., and the outlet temperature was equilibrated at 40-50° C. by fine tuning the emulsion feed rate. The resulting polymer powder was collected in a glass jar attached to the cyclone and subsequently vacuum dried at room temperature to removed residual moisture.

Example 4

Preparation of Exemplary and Comparative Oil Cleansing Formulations

Exemplary oil cleansing formulations in accordance with the present invention and comparative oil cleansing formulations contain the components recited in Table 4.

TABLE 4

Exemplary and Comparative Oil Cleansing Formulations

| Component | INCI Name | Control wt % | F1 wt % | F2 wt % | F3 wt % | F4 wt % | F5 wt % | F6 Wt % | FC 1* wt % | FC 2* wt % | FC 3* wt % | FC 4* wt % |
|---|---|---|---|---|---|---|---|---|---|---|---|---|
| Sunflower Seed Oil+ | Helianthus annuus | 60 | 57 | 57 | 57 | 57 | 57 | 57 | 57 | 57 | 57 | 57 |
| Lumorol K1000++ | MIPA-laureth sulfate/ Cocamide DEA/ Laureth-4 | 30 | 28.5 | 28.5 | 28.5 | 28.5 | 28.5 | 28.5 | 28.5 | 28.5 | 28.5 | 28.5 |
| Rheodol 430V+++ | Sorbeth-30 Tetraoleate | 10 | 9.5 | 9.5 | 9.5 | 9.5 | 9.5 | 9.5 | 9.5 | 9.5 | 9.5 | 9.5 |
| P1 | — | — | 5 | — | — | — | — | — | — | — | — | — |
| P2 | — | — | — | 5 | — | — | — | — | — | — | — | — |
| P3 | — | — | — | — | 5 | — | — | — | — | — | — | — |
| P4 | — | — | — | — | — | 5 | — | — | — | — | — | — |
| P5 | — | — | — | — | — | — | 5 | — | — | — | — | — |
| P6 | — | — | — | — | — | — | — | 5 | — | — | — | — |
| C1 | — | — | — | — | — | — | — | — | 5 | — | — | — |
| C2 | — | — | — | — | — | — | — | — | — | 5 | — | — |
| C3 | — | — | — | — | — | — | — | — | — | — | 5 | — |
| C4 | — | — | — | — | — | — | — | — | — | — | — | 5 |

+Available from Spectrum Chemical
++Available from Zchimmer & Schwarz
+++Available from Kao Chemical
*Comparative Exemplary and comparative oil cleansing formulations were formulated by mixing the exemplary and comparative polymers as prepared in Example 3 together with the other components in the amounts specified in Table 4 under stirring at 500 rpm at 50° C. for 1 hour.

Example 5

Clarity of Exemplary and Comparative Oil Cleansing Formulations

The viscosities of exemplary and comparative oil cleansing formulations as prepared in Example 4 are shown in Table 5.

TABLE 5

Clarity of Exemplary and Comparative Oil Cleansing Formulations

| Sample | Clarity (grayscale value) [0-255] |
|---|---|
| Control | 11 |
| F1 | 14 |
| F2 | 18 |
| F3 | 12 |
| F4 | 16 |
| F5 | 13 |
| F6 | 15 |
| FC1 | Unstable |
| FC2 | Unstable |
| FC3 | Unstable |
| FC4 | Unstable |

The clarity of each sample was evaluated using image analysis of oil gel solution pictures. The oil gel sample formulation was loaded into a 1 mL transparent glass vial and placed in front of a black background. Optical images were captured using side lighting and then analyzed with image recognition software based on grayscale values 0-255 (clear solution having a value of 0). For good oil gel solutions, the grayscale value is typically less than 26. The results demonstrate that the inventive oil cleansing formulations exhibit superior clarity, while the polymer in the comparative oil cleansing formulation aggregated in formulation.

Example 6

Rheology Characterization of Exemplary and Comparative Oil Cleansing Formulations Viscosities of oil cleansing formulations as prepared in Example 4 were measured using a DHR3 TA instrument rheometer with a 50 mm parallel plate geometry (Peltier plate Quartz, 1 mm gap). All measurements were performed at a strain of 2%, within the linear viscoelastic regime. All analyses were performed at 25° C., and isothermal flow sweep was conducted. A logarithmic step ramp method was used ranging over the shear stress of 0.1-1000 Pa with 10 data points per decade after an initial 2 minute equilibration.

Table 6 shows the viscosity versus shear rate rheology profiles for exemplary oil cleansing formulations F1-F5 against the Control, respectively.

TABLE 6

Viscosity of Exemplary Oil Cleansing Formulations

| Sample | Viscosity at 0.2/S (shear rate) [Pa · S] | Viscosity at 100/S (shear rate) [Pa · S] |
|---|---|---|
| Control | 0.14 | 0.14 |
| F1 | 2.93 | 1.05 |
| F2 | 0.94 | 0.64 |
| F3 | 2.10 | 0.44 |
| F4 | 2.06 | 0.70 |
| F5 | 3.24 | 0.61 |
| F6 | 1.65 | 1.02 |

The exemplary oil cleansing formulations demonstrated an increase in viscosity and shear thinning behavior, which is highly desirable for oil cleansing formulations.

What is claimed is:

1. A personal care composition comprising:
   (a) at least one cosmetically acceptable hydrophobic ester oil, wherein the cosmetically acceptable hydrophobic ester oil comprises one or more aliphatic $C_8$-$C_{24}$ alkyl triglycerides;
   (b) at least one surfactant selected from the group consisting of nonionic surfactants, anionic surfactants, and mixtures thereof; and
   (c) one or more polymers comprising polymerized structural units of
      (i) 84.5 to 91.45 weight % of $C_4$-$C_8$ (meth)acrylate monomers, wherein the $C_4$-$C_8$ (meth)acrylate monomers comprise i-butyl methacrylate and ethyhexyl methacrylate in a ratio of from 3:2 to 2:3,
      (ii) 0.5 to 5 weight % of (meth)acrylic acid monomer,
      (iii) 3.75 to 14 weight % of (methoxy) poly(ethylene glycol) methacrylates, and
      (iv) 0.01 to 2 weight % of at least one crosslinker.

2. The personal care composition of claim 1, wherein the at least one surfactant comprises a nonionic surfactant and an anionic alkyl ether sulfate surfactant, wherein the nonionic surfactant has a hydrophile-lipophile balance value of from 7 to 14.

3. The personal care composition of claim 2, wherein the nonionic surfactant has a hydrophile-lipophile balance value of from 9 to 12.

4. The personal care composition of claim 2, wherein the anionic alkyl ether sulfate surfactant comprises at least one of a triethanolamine salt and a monoisopropanolamine salt.

5. The personal care composition of claim 1, wherein the (methoxy) poly(ethylene glycol) methacrylates have a weight average molecular weight of from 200 to 2300.

6. The personal care composition of claim 1, wherein the (methoxy) poly(ethylene glycol) methacrylates have a weight average molecular weight of from 300 to 600.

7. The personal care composition of claim 1, wherein the crosslinker is selected from the group consisting of trimethylolpropane trimethacrylate, trimethylolpropane diallyl ether, ethylene glycol dimethylacrylate, polypropylene glycol dmiethacrylate, and combinations thereof.

* * * * *